US00PP13982P29

(12) United States Plant Patent
Hanes

(10) Patent No.: US PP13,982 P2
(45) Date of Patent: Jul. 15, 2003

(54) VERBENA PLANT NAMED 'LAN BRIGHT PINK'

(75) Inventor: Mitchell Eugene Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 10/057,924

(22) Filed: Jan. 29, 2002

(51) Int. Cl.[7] ..... A01H 5/00
(52) U.S. Cl. ..... Plt./308
(58) Field of Search ..... Plt./308

*Primary Examiner*—Bruce R. Campell
*Assistant Examiner*—Annette H. Para
(74) *Attorney, Agent, or Firm*—Jondle & Associates PC

(57) ABSTRACT

A verbena cultivar particularly distinguished by bright pink colored flowers, vigorous growth and semi-trailing habit.

1 Drawing Sheet

GENUS AND SPECIES

*Verbena hybrida.*

VARIETY DENOMINATION

'Lan Bright Pink'.

BACKGROUND OF THE NEW PLANT

The present invention comprises a new and distinct cultivar of verbena, botanically known as *Verbena hybrida,* and hereinafter referred to by the cultivar name 'Lan Bright Pink'. The new cultivar is asexually reproduced from vegetative cuttings and tissue culture resulting from the cross of the seed/pod parent 98-767-1, an unnamed and unpatented red proprietary line and the pollen parent 'Temari Bright Pink' (U.S. Plant Pat. No. 11,037), a commercial line.

'Lan Bright Pink' is a product of a planned breeding program intended to create new verbena cultivars with bright pink colored flowers, dark green foliage, vigorous growth and semi-trailing habit.

The new cultivar was created in 1999 in Gilroy, Calif. and has been asexually reproduced repeatedly by vegetative cuttings and tissue culture in Gilroy, Calif. over a two year period. It has also been trialed at Gilroy, Calif.; Alberta, Canada, Litchfield, Mich. and Andijk, The Netherlands. The present invention has been found to retain its distinctive characteristics through successive propagations; and this novelty is firmly fixed.

DESCRIPTION OF PHOTOGRAPH

This new verbena plant is illustrated by the accompanying photograph which shows blooms, buds, and foliage of the plant in full color, the colors shown being as true as can be reasonably obtained by conventional photographic procedures.

The drawing shows overall plant habit and the mature inflorescence.

DESCRIPTION OF THE NEW CULTIVAR

The following detailed descriptions set forth the distinctive characteristics of 'Lan Bright Pink'. The data which defines these characteristics were collected from asexual reproductions carried out in Alberta Canada. The plant history was taken on 11 week old plants grown in 4 inch pots, blossomed under natural light in a greenhouse and color readings were taken in the greenhouse in Alberta Canada. Color references are primarily to The R.H.S. Colour Chart of The Royal Horticultural Society of London (R.H.S.).

THE PLANT

Classification:
*Botanical.*—*Verbena hybrida.*
*Commercial.*—Verbena.
Form: Low trailing annual, decumbent.
Growth and branching habit: Vigorous growing, dense basal branching; low trailing habit.
Height: From soil level to top of blooms: Approximately 7 cm.
Width: Approximately 53 cm.
Time to produce a finished flowering plant: 11 weeks.
Outdoor plant performance: Typical bedding plant culture, full sun in the garden, hanging baskets or container plants.
Time to initiate roots: Approximately 4 days in the greenhouse.
Time to develop roots: Approximately 7 days in the greenhouse.
Root description: Fibrous, fleshy, white.

THE LEAVES

Length: 2.9–5.0 cm.
Width: 2.5–3.6 cm.
Leaf blade shape: Tripartite-pinnatifid; segments linear or narrowly oblanceolate.
Leaf margin: Irregular, crenately incised, with secondary sharp teeth.
Apex aspect: Obtuse.
Base aspect: Cuneate.
Foliage color: Upper surface — Yellow-green RHS 147A; Lower surface is yellow-green RHS 147B.
Texture: Moderately hairy.
Venation: Pinnatifid, pubescent.
Venation color: Upper surface is yellow-green RHS 146C; lower surface is yellow-green RHS 144C.
Petiole length: 8 mm.
Petiole diameter: 1.2 mm.
Petiole color: Upper surface is yellow-green RHS 146C; lower surface is yellow-green RHS 146D.

THE STEM

Length: 13–28 cm.
Diameter: 2.0–3.0 mm.
Internode length: 2.0–3.5 cm.
Color: Upper surface is yellow-green RHS 144A; lower surface is yellow-green RHS 144B.
Texture: Moderately hairy.
Stem anthocyanin: Moderate anthocyanin on stem, with stronger intensity along stem edge.

THE BUD

Shape: Linear.
Diameter: 2 mm.
Length: 12 mm.
Color at tight bud: Red-purple RHS N57A.

THE FLOWER

Blooming habit: Continuous throughout the growing season.
Inflorescence type: Spike.
Spikes per plant: 20–25.
Spike diameter: Approximately 5.7 cm.
Spike depth: Approximately 3.1 cm.
Peduncle length: 2.5–5.2 cm.
Peduncle diameter: 2 mm.
Peduncle color: Yellow-green RHS 144A.
Peduncle texture: Moderately pubescent.
Flower color: Upper petal surface is red-purple RHS N57A; Lower petal surface is red-purple that is between RHS 57C and 57D.
Flower eye size and color: Small eye at base of petal; white RHS 155A with yellow RHS 4C at center.
Floret form: Salverform; sessile on spikes.
Floret (limb) diameter: Approximately 18.7 mm.
Corolla tube length: Approximately 20 mm.
Number florets per spike: 25–35 (closed to fully open florets).
Number of petals: Gamopetalous, five lobed.
Petal size:
*Length of one lobe.*—10 mm.
*Width of one lobe.*—9 mm.
Petal lobe shape: Obcordate.
Petal apex shape: Deeply emarginate.
Petal base shape: Fused.
Petal margin: Entire.
Petal texture: Smooth with fine pubescence.
Sepals: Five sepals whose margins are fused to each other along their length with a transparent membrane of less than 1 mm in width with one smaller sepal (5 mm) attached to the base of the calyx.
Calyx length: Approximately 12 mm.
Calyx width: Approximately 5 mm.
Calyx shape: Linear.
Calyx apex: Acute.
Calyx color: Yellow-green RHS 137C.
Lastingness of individual blooms: One week.
Fragrance: None.

THE REPRODUCTIVE ORGANS

Stamens: Anthers and filaments fused to upper half of corolla tube; four anthers with two pollen sacs per anther.
Pollen amount and color: Moderate, yellow RHS 5D.
Pistil: One style approximately 18 mm; transparent to yellow RHS 1D throughout length with yellow-green RHS 144C near tip, slightly curved at the tip with one stigma yellow-green RHS 144A.
Fruit seed set: Does not freely set seed but can produce 4 narrow nutlets, approximately 4 mm long; colored grey-brown RHS 199D and enclosed in the dried calyx

DISEASE AND INSECT RESISTANCE

Tolerant to mildew.

COMPARISON WITH PARENTAL CULTIVARS

When the instant plant is compared to male parent 'Temari Bright Pink' (U.S. Plant Pat. No. 11,037) the 'Lan Bright Pink' has leaves that are longer and wider than 'Temari Bright Pink'. The stem on 'Lan Bright Pink' is less pubescent and little in color than 'Temari Bright Pink'. 'Lan Bright Pink' has a leaf shape that is tripartite while 'Temari Bright Pink' is broadly ovate. 'Lan Bright Pink' has a greater flower density than 'Temari Bright Pink'. The floret color on the upperside of the petals on 'Lan Bright Pink' are paler than 'Temari Bright Pink'. Additionally, the flower diameter 'Lan Bright Pink' is a little less than that of 'Temari Bright Pink'.

When 'Lan Bright Pink' is compared to female parent 98-767-1 'Lan Bright Pink' has broader leaves than 98-767-1. 'Lan Bright Pink' has a pink flower as compared to red for 98-767-1 and 'Lan Bright Pink' is a more vigorous plant and 98-767-1 is a compact growing plant.

I claim:

1. A new and distinct cultivar of verbena as shown and described herein.

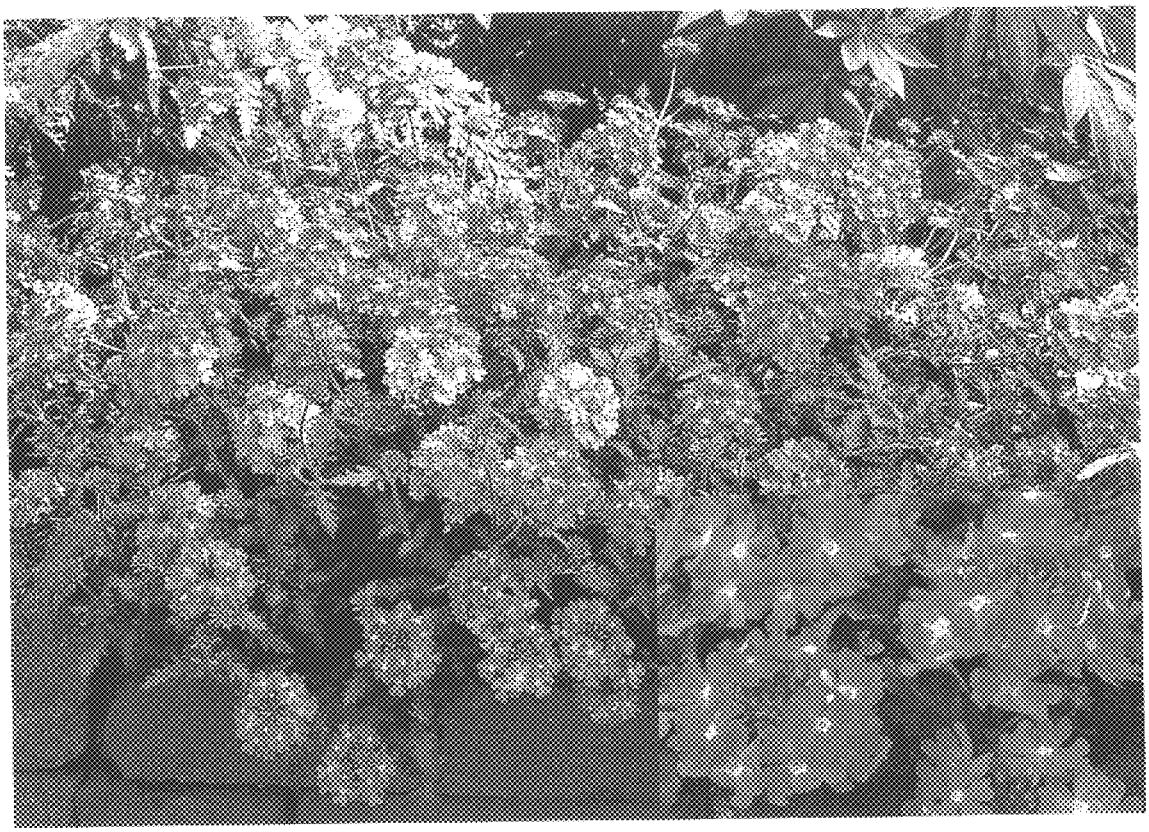

* * * * *